(12) United States Patent
Nakagawa et al.

(10) Patent No.: US 11,667,875 B1
(45) Date of Patent: Jun. 6, 2023

(54) MICROFLUIDIC DEVICES AND USES THEREOF

(71) Applicant: ThinkCyte, Inc., Tokyo (JP)

(72) Inventors: Keiji Nakagawa, Tokyo (JP); Yoko Kawamura, Tokyo (JP)

(73) Assignee: ThinkCyte, Inc., Tokyo (JP)

( * ) Notice: Subject to any disclaimer, the term of this patent is extended or adjusted under 35 U.S.C. 154(b) by 740 days.

(21) Appl. No.: 16/562,262

(22) Filed: Sep. 5, 2019

Related U.S. Application Data

(60) Provisional application No. 62/727,966, filed on Sep. 6, 2018.

(51) Int. Cl.
| | |
|---|---|
| *C12N 15/10* | (2006.01) |
| *B01L 3/00* | (2006.01) |
| *C12M 3/06* | (2006.01) |
| *C12M 1/00* | (2006.01) |
| *B01F 33/30* | (2022.01) |

(52) U.S. Cl.
CPC ............. *C12M 23/16* (2013.01); *B01F 33/30* (2022.01); *C12M 23/20* (2013.01)

(58) Field of Classification Search
CPC ......... C12M 23/16; C12M 23/20; B01F 33/30
See application file for complete search history.

(56) References Cited

U.S. PATENT DOCUMENTS

2018/0208412 A1\* 7/2018 Gilbert .................. B07C 5/00

\* cited by examiner

*Primary Examiner* — Jennifer Wecker
*Assistant Examiner* — Oyeleye Alexander Alabi
(74) *Attorney, Agent, or Firm* — Wilson Sonsini Goodrich & Rosati

(57) ABSTRACT

The present disclosure provides systems, devices, and methods for flow focusing in a microfluidic device. Flow focusing may be used in detection of objects, for example cells, in a stream of fluid passing through a fluidic device. The systems and devices may comprise a flow channel positioned between two sheath channels configured to direct fluid across the flow channel. Flow focusing microfluidic systems and devices disclosed herein may be robust to alignment errors. Systems and devices of the present disclosure may reduce the displacement of flow from the intended locations due to alignment errors. Also disclosed herein are methods for using such microfluidic systems and devices.

24 Claims, 9 Drawing Sheets
(6 of 9 Drawing Sheet(s) Filed in Color)

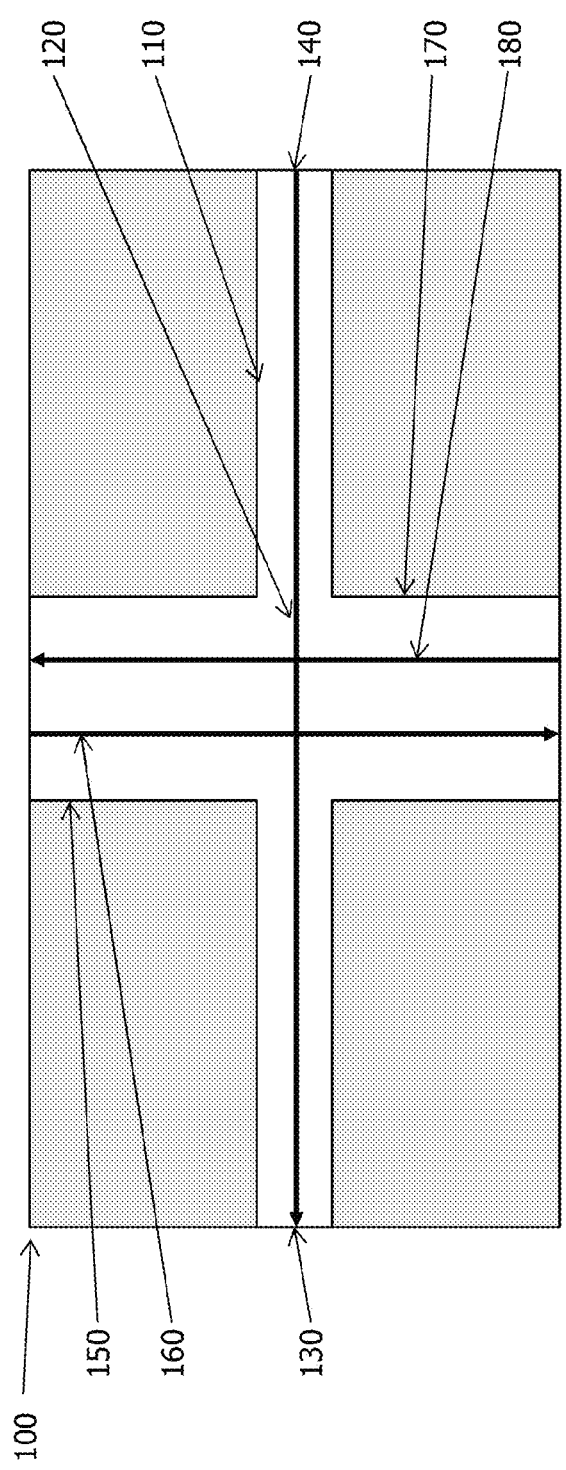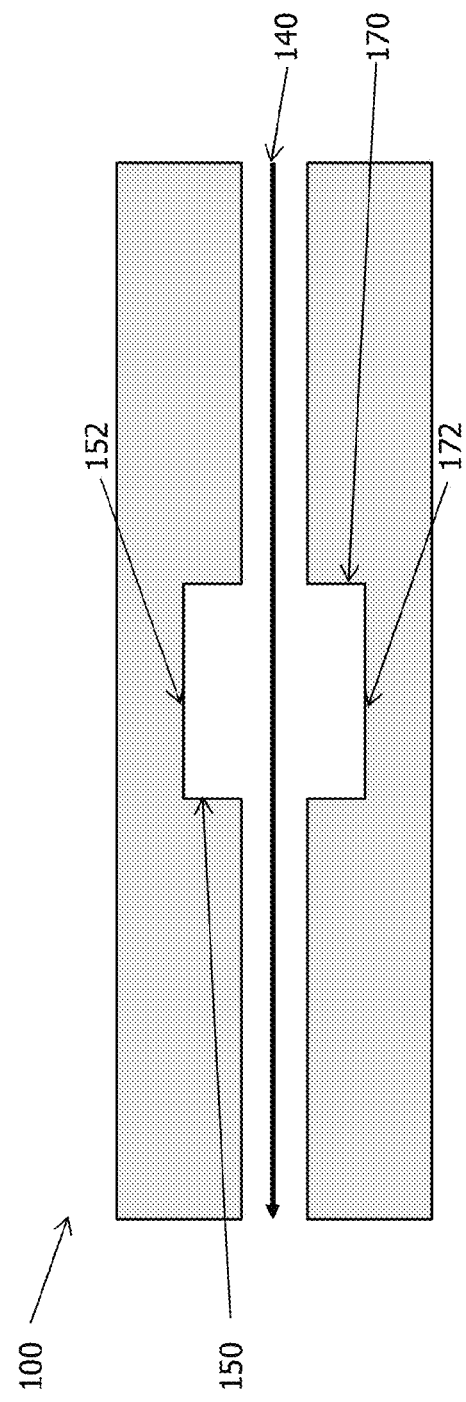

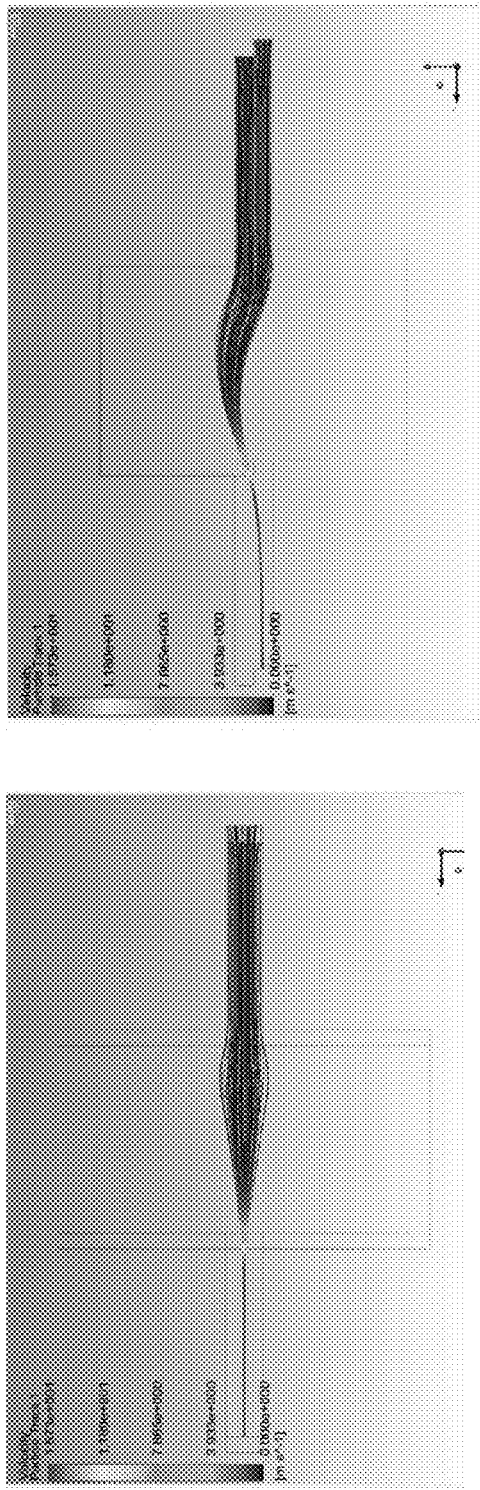
FIG. 1E
FIG. 1F
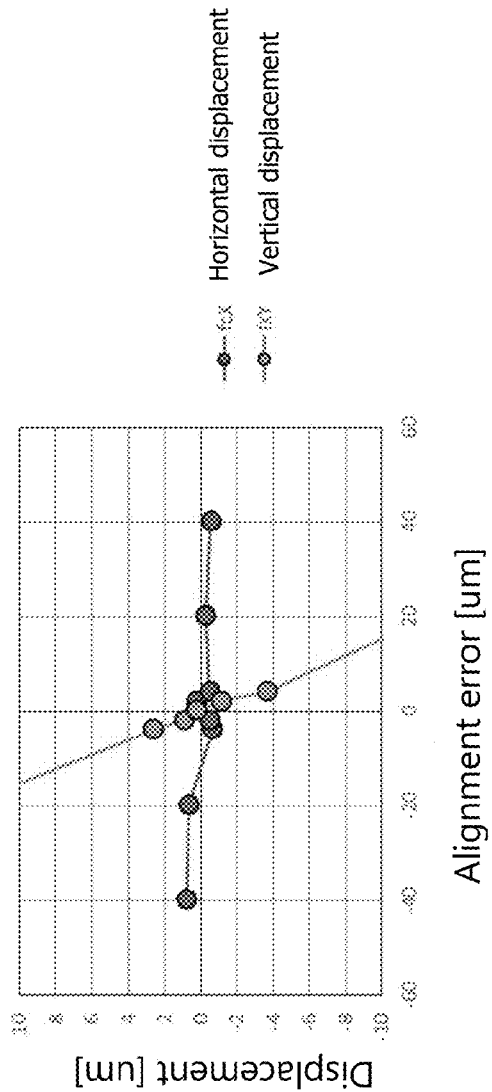
FIG. 1G

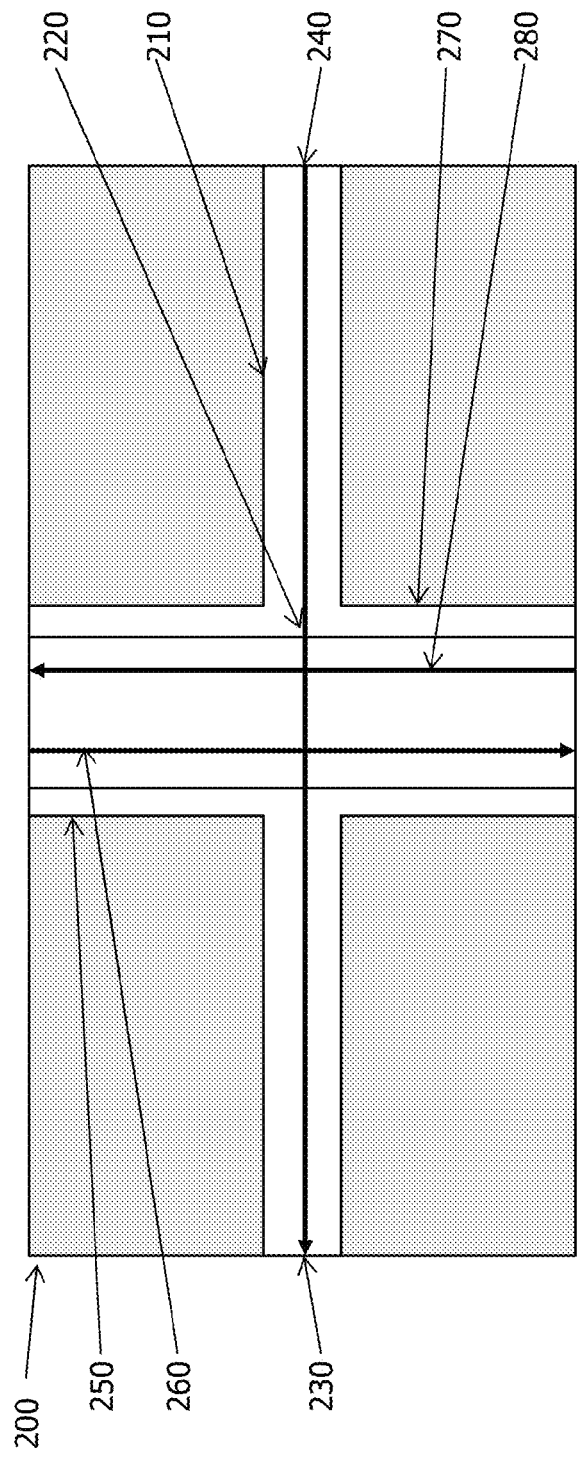
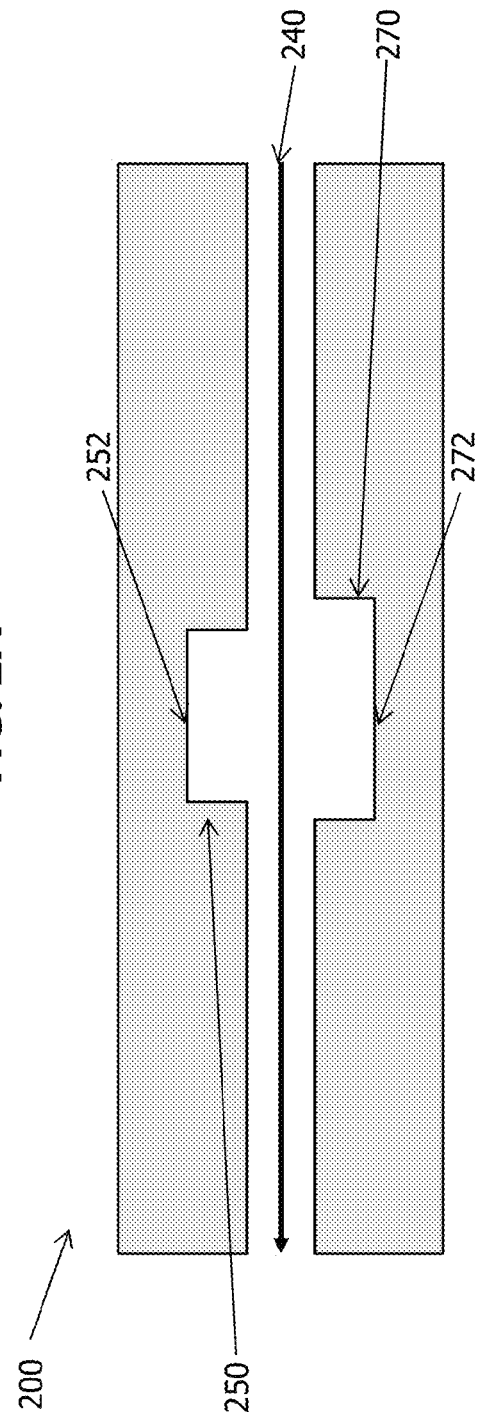
FIG. 2A
FIG. 2B

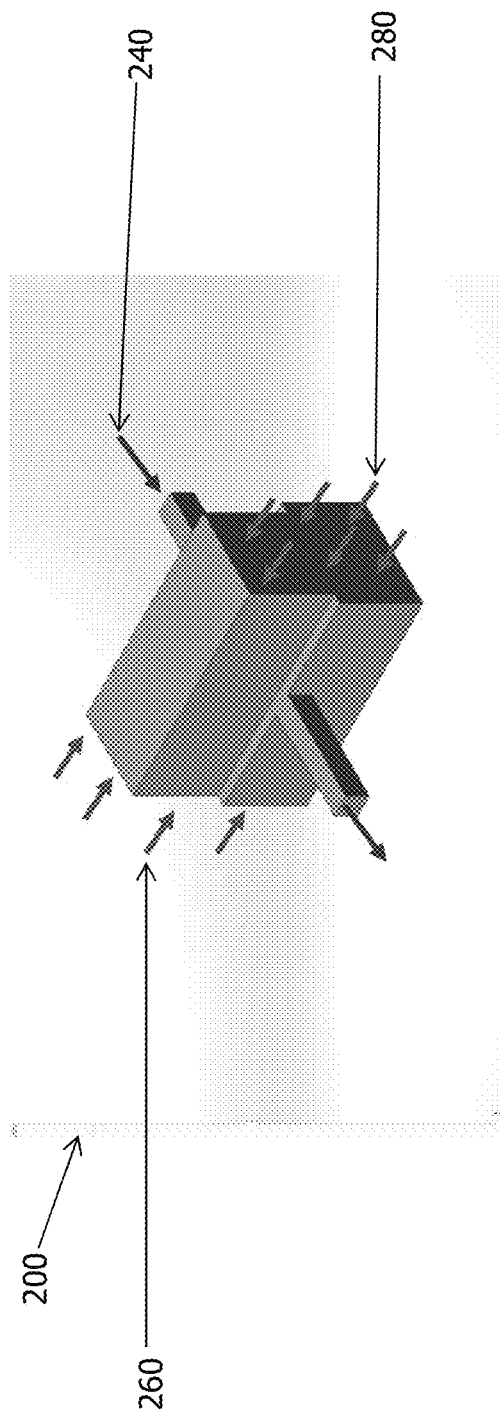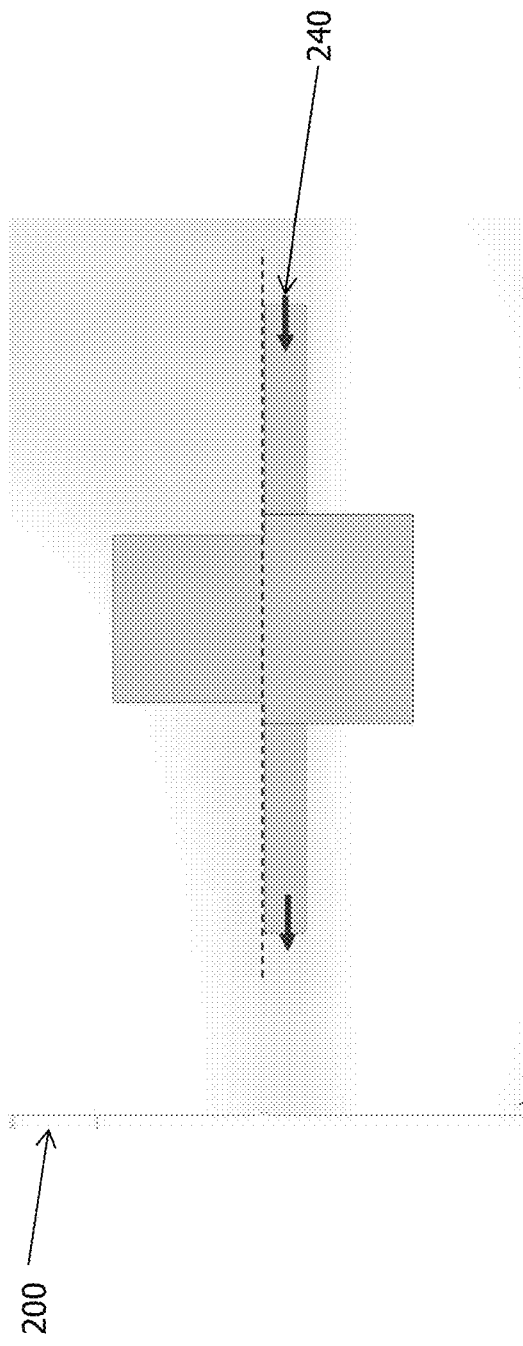

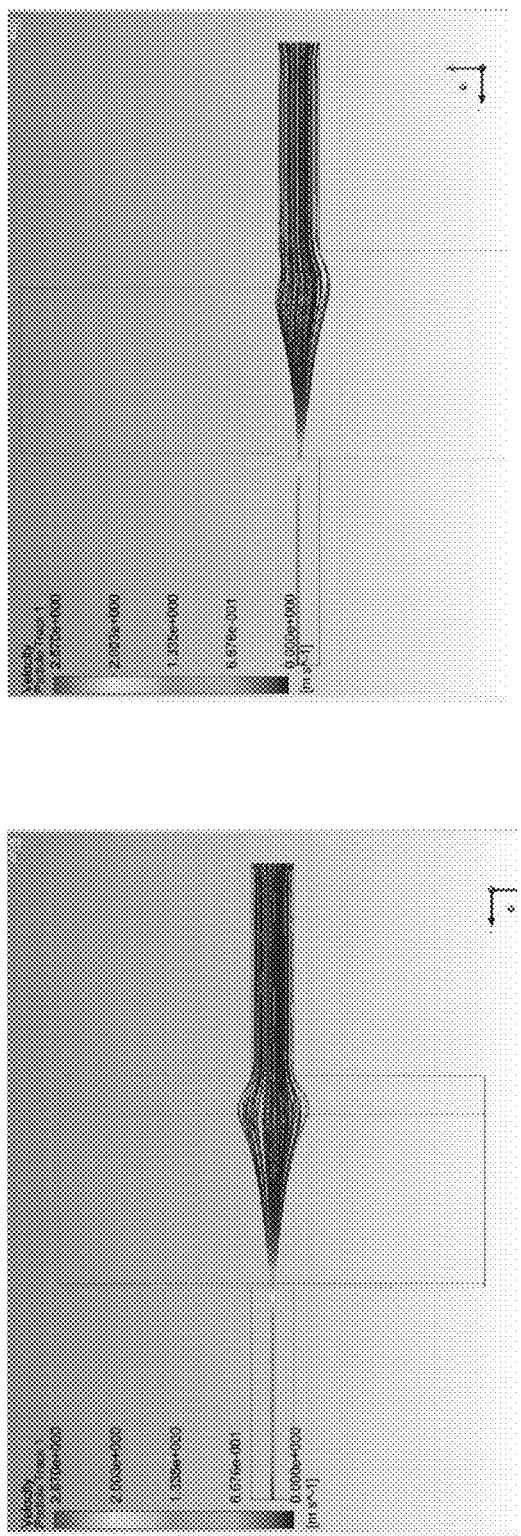
FIG. 2E
FIG. 2F
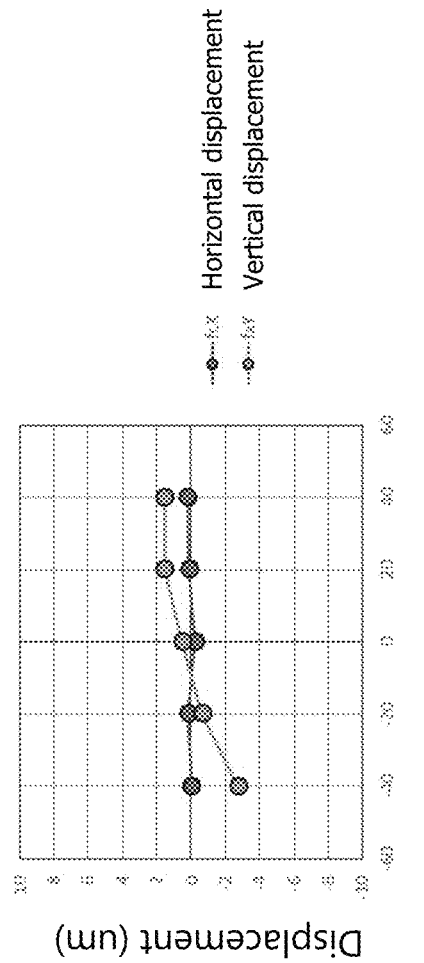
FIG. 2G

MICROFLUIDIC DEVICES AND USES THEREOF

CROSS-REFERENCE

This application claims the benefit of U.S. Provisional Patent Application No. 62/727,966, entitled "FLOW FOCUSING MICROFLUIDIC DEVICE", filed Sep. 6, 2018, which is herein incorporated by reference in its entirety.

BACKGROUND

Hydrodynamic focusing may be used for numerous applications, such as microfluidic mixing, separations, sensors, cell analysis, flow cytometry, diffusion-controlled chemical reactions and microfabrication. Hydrodynamic focusing may occur when fluids with different velocities are injected side by side.

Flow focusing microfluidic devices may find use in a number of applications, such as flow cytometry, which may be employed in cell counting, cell sorting, biomarker detection or protein engineering, such as by suspending cells in a stream of fluid and passing them through an electronic detection apparatus.

SUMMARY

Prior flow focusing microfluidic devices may be adversely affected by alignment errors, such as those which may arise during device manufacturing. Thus, recognized herein is a need for flow focusing microfluidic devices that may be robust to alignment errors.

The present disclosure provides flow focusing microfluidic devices that may be robust to alignment errors, in addition to methods for using such microfluidic devices. Such devices may include a flow channel that may be operated in a manner that causes a fluid that flows through the flow channel to fluidically contact first and second sheath fluids that flow through first and second sheath channels to hydrodynamically focus the fluid. The first and second sheath channels may have different cross-sections. For instance, the first and second sheath channels may have different widths. The different sheath channel cross-sections or widths may make a flow focusing microfluidic device having such sheath channels more robust to alignment errors than other flow focusing microfluidic devices.

In an aspect, a system for fluid flow focusing may comprise: a flow channel configured to direct a fluid from a first point to a second point of a fluid flow path; a first sheath channel intersecting said flow channel between said first point and said second point, wherein said first sheath channel is configured to direct a first sheath fluid across said flow channel; and a second sheath channel intersecting said flow channel between said first point and said second point, wherein said second sheath channel has a different cross-section than said first sheath channel, and wherein said second sheath channel is configured to direct a second sheath fluid across said flow channel.

The system may further comprise a fluid flow unit coupled to one or more of said flow channel, said first sheath channel, and said second sheath channel, wherein said fluid flow unit is configured to direct one or more of said fluid through said flow channel, said first sheath fluid through said first sheath channel, and said second sheath fluid through said second sheath channel. Said fluid flow unit may comprise one or more pumps and/or one or more compressors.

Said flow channel and said first and second sheath channels may be arranged in a vertically stacked configuration such that said flow channel is located between said first and second sheath channels.

Said flow channel may be orthogonal to one or more of said first and second sheath channels.

Said fluid may be configured to fluidically interact with said first and second sheath fluids. Said fluid may be configured to fluidically contact said first and second sheath fluids. Said first and second sheath fluids may be configured to hydrodynamically focus said fluid.

Said flow channel may comprise a flow channel width of at most 2 millimeters (mm). Said first sheath channel width and said second channel width may be at most 20 millimeters (mm).

Said flow channel and said first sheath channel may be formed on a first substrate and said second sheath channel may be formed on a second substrate that is different from said first substrate. Said first and second substrates may comprise a material individually selected from the group consisting of: glasses, semiconductors, elastomers, plastics, and metals. Said first and second substrates may comprise a material individually selected from the group consisting of: glass, silicon, polydimethylsiloxane (PDMS), poly(methyl methacrylate) (PMMA), polycarbonate, cyclo-olefin copolymer (COC), cyclo-olefin polymer (COP), and aluminum.

Said first sheath fluid and said second sheath fluid may be the same fluid.

Said first sheath channel may be adjacent to said second sheath channel.

The system may further comprise one or more additional sheath channels between said first sheath channel and said second sheath channel, wherein each of said one or more additional sheath channels intersects said flow channel between said first point and said second point.

In another aspect, a method for fluid flow focusing may comprise: (a) providing (i) a flow channel comprising a fluid flow path having a first point and second point, (ii) a first sheath channel intersecting said flow channel between said first point and said second point, and (iii) a second sheath channel intersecting said flow channel between said first point and said second point, wherein said second sheath channel has a different cross-section than said first sheath channel; (b) subjecting a fluid to flow along said fluid flow path of said flow channel; and (c) subjecting (1) a first sheath fluid to flow along said first sheath channel and across said flow channel and (2) a second sheath fluid to flow along said second sheath channel and across said flow channel.

Said first and second sheath fluids may hydrodynamically focus said fluid.

In another aspect, a method for manufacturing a device for fluid flow focusing may comprise using one or more members selected from the group consisting of micromachining, fabrication, three-dimensional printing and injection molding to generate said device comprising: a flow channel configured to direct a fluid from a first point to a second point of a fluid flow path; a first sheath channel intersecting said flow channel between said first point and said second point, wherein said first sheath channel is configured to direct a first sheath fluid across said flow channel; and a second sheath channel intersecting said flow channel between said first point and said second point, wherein said second sheath channel has a different cross-section than said first sheath channel, and wherein said second sheath channel is configured to direct a second sheath fluid across said flow channel.

The method may further comprise (i) providing a first substrate and a second substrate, wherein said first substrate comprises said first sheath channel and said second substrate comprises said second sheath channel, and (ii) bringing said first substrate in contact with said second substrate. Said first substrate may comprise a first portion of said flow channel and said second substrate may comprise a second portion of said flow channel. Said first substrate may comprise said flow channel. Said second substrate may comprise said flow channel.

In an aspect, a system for fluid flow focusing may comprise: a flow channel configured to direct a fluid from a first point to a second point of a fluid flow path; a first sheath channel intersecting said flow channel between said first point and said second point, wherein said first sheath channel is configured to direct a first sheath fluid across said flow channel; and a second sheath channel intersecting said flow channel between said first point and said second point, wherein said second sheath channel has a different cross-section than said first sheath channel, and wherein said second sheath channel is configured to direct a second sheath fluid across said flow channel.

Said fluid flow path may be vertically displaced no more than 8 µm from a center line of said flow channel when said first sheath channel and said second sheath channel are misaligned by no more than 40 µm.

In another aspect, a system for fluid flow focusing may comprise a fluid flow unit coupled to one or more of said flow channel, said first sheath channel, and said second sheath channel, wherein said fluid flow unit is configured to direct one or more of said fluid through said flow channel, said first sheath fluid through said first sheath channel, and said second sheath fluid through said second sheath channel.

Said fluid flow unit may comprise one or more pumps, one or more compressors, or both. Said flow channel and said first and second sheath channels may be arranged in a vertically stacked configuration such that said flow channel is located between said first sheath channel and said second sheath channel. Said flow channel may be orthogonal to said first sheath channel, said second sheath channel, or both. Said fluid may be configured to fluidically interact with or contact said first sheath fluid and said second sheath fluid. Said first sheath fluid and said second sheath fluid may be configured to hydrodynamically focus said fluid.

Said flow channel may comprise a flow channel width of at most 2 millimeters (mm). Said first sheath channel may comprise a first sheath channel width, and said second sheath channel comprises a second sheath channel width, and said first sheath channel width, said second sheath channel width, or both are at most 20 millimeters (mm). Said first sheath channel may be formed on a first substrate and said second sheath channel is formed on a second substrate that is different from said first substrate.

In another aspect, a first portion of the flow channel may be formed on said first substrate and a second portion of the flow channel is formed on said second substrate. Said flow channel may be formed on said first substrate. Said flow channel may be formed on said second substrate. Said first substrate and said second substrate may comprise a material individually selected from the group consisting of: glasses, semiconductors, elastomers, plastics, and metals. Said first substrate and said second substrate may comprise a material individually selected from the group consisting of: glass, silicon, polydimethylsiloxane (PDMS), poly(methyl methacrylate) (PMMA), polycarbonate, cyclo-olefin copolymer (COC), cyclo-olefin polymer (COP), and aluminum.

Said first sheath fluid and said second sheath fluid may be the same fluid. Said first sheath channel may be adjacent to said second sheath channel.

In another aspect, a system for fluid flow focusing may comprise one or more additional sheath channels between the first sheath channel and said second sheath channel, wherein each of said one or more additional sheath channels intersects said flow channel between said first point and said second point. Said system may be manufactured using one or more methods selected from the group consisting of micromachining, three-dimensional printing and injection molding.

In an aspect, a method for fluid flow focusing may comprise: providing a system comprising (i) a flow channel comprising a fluid flow path having a first point and second point, (ii) a first sheath channel intersecting said flow channel between said first point and said second point, and (iii) a second sheath channel intersecting said flow channel between said first point and said second point, wherein said second sheath channel has a different cross-section than said first sheath channel; subjecting a fluid to flow along said fluid flow path of said flow channel; and subjecting (1) a first sheath fluid to flow along said first sheath channel and across said flow channel and (2) a second sheath fluid to flow along said second sheath channel and across said flow channel.

Said first sheath fluid and said second sheath fluid may flow in opposite directions. Said first sheath fluid and said second sheath fluid may hydrodynamically focus said fluid.

In an aspect, a system for reducing the displacement of flow due to alignment errors may comprise: a flow channel; and a first sheath channel and a second sheath channel which intersects said flow channel, wherein said first sheath channel has a different cross section to said second sheath channel thereby reducing the displacement of flow due to alignment errors.

In an aspect, a method for reducing the displacement of flow due to alignment errors may comprise: providing a system comprising (i) a flow cannel; and (ii) a first sheath channel and a second sheath channel which intersects said flow channel, wherein said first sheath channel has a different cross section to said second sheath channel, flowing a fluid along said flow channel; and flowing a first sheath fluid along said first sheath channel and across the intersection of said flow channel and flowing a second sheath fluid along said second sheath channel and across the intersection of said flow channel, thereby reducing the displacement of said fluid along said flow channel due to alignment errors.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A shows a top view of a schematic for a flow focusing microfluidic device comprising first and second sheath channels having equal cross-sections.

FIG. 1B shows a side view of a schematic for a flow focusing microfluidic device comprising first and second sheath channels having equal cross-sections.

FIG. 1E shows simulated horizontal displacement of flow from an intended location due to misalignments in an exemplary flow focusing microfluidic device comprising first and second sheath channels having equal cross-sections.

FIG. 1F shows simulated vertical displacement of flow from an intended location due to alignment error in an exemplary flow focusing microfluidic device comprising first and second sheath channels having equal cross-sections.

FIG. 1G shows a graph of simulated horizontal and vertical displacements of flow from an intended location as a function of alignment error in an exemplary flow focusing microfluidic device comprising first and second sheath channels having equal cross-sections.

FIG. 2A shows a top view of a schematic for a flow focusing microfluidic device comprising first and second sheath channels having different cross-sections.

FIG. 2B shows a side view of a schematic for a flow focusing microfluidic device comprising first and second sheath channels having different cross-sections.

FIG. 2C shows an isometric view of an exemplary flow focusing microfluidic device comprising first and second sheath channels having different cross-sections.

FIG. 2D shows a side view of an exemplary flow focusing microfluidic device comprising first and second sheath channels having different cross-sections.

FIG. 2E shows simulated horizontal displacement of flow from an intended location due to misalignments in an exemplary flow focusing microfluidic device comprising first and second sheath channels having different cross-sections.

FIG. 2F shows simulated vertical displacement of flow from an intended location due to alignment error in an exemplary flow focusing microfluidic device comprising first and second sheath channels having different cross-sections.

FIG. 2G shows a graph of simulated horizontal and vertical displacements of flow from an intended location as a function of alignment error in an exemplary flow focusing microfluidic device comprising first and second sheath channels having different cross-sections.

DETAILED DESCRIPTION

Figure 1C:
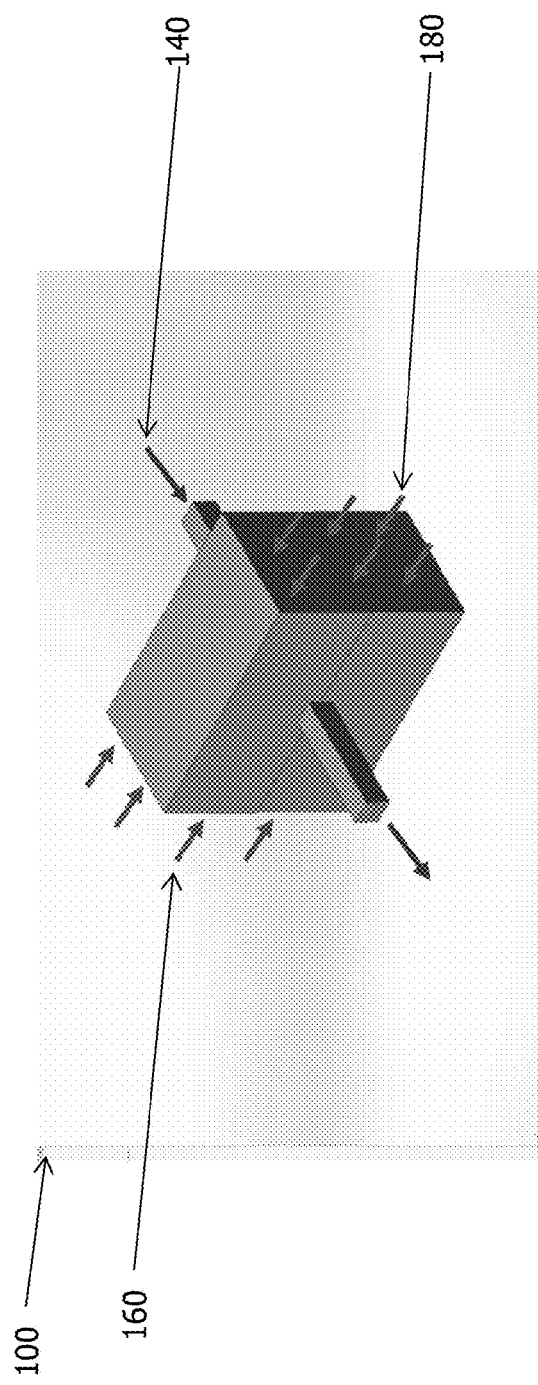
FIG. 1C shows an isometric view of an exemplary flow focusing microfluidic device comprising first and second sheath channels having equal cross-sections.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" refers to an amount that is near the stated amount by about 10%, 5%, or 1%, including increments therein. For example, "about" or "approximately" can mean a range including the particular value and ranging from 10% below that particular value and spanning to 10% above that particular value.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

In an aspect, the present disclosure provides systems for fluid flow focusing. A system for fluid flow focusing may comprise a flow channel configured to direct a fluid from a first point to a second point of a fluid flow path. The system may further include a first sheath channel intersecting the flow channel between the first point and the second point, and a second sheath channel intersecting the flow channel between the first point and the second point. The first sheath channel may be configured to direct a first sheath fluid across the flow channel. The second sheath channel may be configured to direct a second sheath fluid across the flow channel. The second sheath channel may have a different cross-section than the first sheath channel. The second sheath channel may have a different width than the first sheath channel, a different height than the first sheath channel, or both. The second sheath channel may have a different height and a different width than the first sheath channel, and the same cross-sectional area as the first sheath channel.

In another aspect, the present disclosure provides a method for fluid flow focusing, comprising providing (i) a flow channel comprising a fluid flow path having a first point and second point, (ii) a first sheath channel intersecting the flow channel between the first point and the second point, and (iii) a second sheath channel intersecting the flow channel between the first point and the second point, wherein the second sheath channel has a different cross-section than the first sheath channel. Next, a fluid may be subjected to flow along the fluid flow path of the flow channel. Next, (1) a first sheath fluid may be subjected to flow along the first sheath channel and across the flow channel and (2) a second sheath fluid may be subjected to flow along the second sheath channel and across the flow channel.

Reference will now be made to the figures, wherein like numerals refer to like characters throughout. It will be appreciated that the figures are not necessarily drawn to scale.

FIG. 1A shows a top view of a schematic of a flow focusing microfluidic device 100 comprising first and second sheath channels having equal cross-sections. The flow focusing microfluidic device 100 may comprise a flow channel 110 configured to direct a fluid from a first point 120 to a second point 130 of a fluid flow path 140. The flow focusing microfluidic device 100 may further comprise a first sheath channel 150 intersecting the flow channel between the first and second points. The first sheath channel may be configured to direct a first sheath fluid along a first sheath flow path 160 across the flow channel. The flow focusing microfluidic device 100 may further comprise a second sheath channel 170 intersecting the flow channel between the first and second points. The second sheath channel may be configured to direct a second sheath fluid along a second sheath flow path 180 across the flow channel. In some aspects, the first sheath channel and the second sheath channel may be orthogonal to the flow channel. As shown in FIG. 1A, the first and second sheath fluids may cross the flow channel in opposite directions. The first sheath fluid may flow in a direction orthogonal to the flow channel. The second sheath fluid may flow in a direction orthogonal to the flow channel.

FIG. 1B shows a side view of the schematic for the flow focusing microfluidic device 100. As shown in FIG. 1B, the flow channel 110 and first and second sheath channels 150 and 170, respectively, may be arranged in a vertically stacked configuration such that the flow channel is located between the first and second sheath channels (e.g., the first sheath channel may be located above the flow channel and the flow channel may be located above the second sheath channel). The first sheath channel may have a first cross-section and the second sheath channel may have a second cross-section. The first and second cross-sections may be equal. The first sheath channel may have a first width 152 and the second sheath channel may have a second width 172. The first and second widths may be equal.

FIG. 1C shows an isometric view of the flow focusing microfluidic device 100.

Figure 1D:
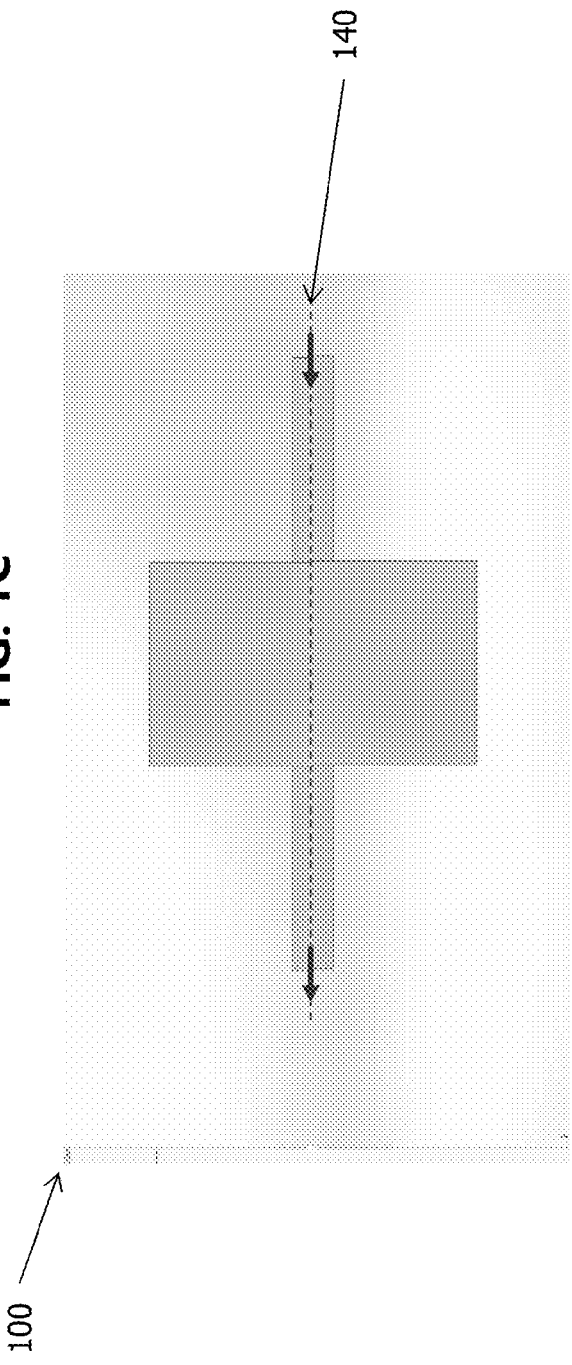
FIG. 1D shows a side view of an exemplary flow focusing microfluidic device comprising first and second sheath channels having equal cross-sections.

FIG. 1D shows a side view of the flow focusing microfluidic device 100.

The first and second sheath channels may be well-aligned, such that the first sheath channel is positioned directly above the second sheath channel, as depicted in FIG. 1B. However, manufacturing tolerances may result in alignment errors of the first or second sheath, or both. Such alignment errors may have a negative effect on the performance of the flow focusing microfluidic device 100.

FIG. 1E shows simulated horizontal displacement of flow from an intended location due to misalignments in the flow focusing microfluidic device 100. For the simulation depicted in FIG. 1E, the first and second channels had an alignment error of 40 micrometers (μm). As depicted in FIG. 1E, the fluid flows along the flow path from the right. Upon interacting with the first and second sheath fluids, the fluid is highly focused on the left. Some displacement from the intended location (the center of the flow channel) may be evident, as shown by an offset of the fluid flow lines from the zero point of the y-axis, representing the center of the flow channel, on the left side of the plot in FIG. 1E.

FIG. 1F shows simulated vertical displacement of flow from an intended location due to alignment error in the flow focusing microfluidic device 100. For the simulation depicted in FIG. 1F, the first and second channels had an alignment error of 40 μm. As depicted in FIG. 1F, the fluid flows along the flow path from the right. Upon interacting with the first and second sheath fluids, the fluid is highly focused on the left. However, a displacement from the intended location (the center of the flow channel) may be evident, as shown by an offset of the fluid flow lines from the zero point of the y-axis, representing the center of the flow channel, on the left side of the plot in FIG. 1F. The resulting focused flow is below the center of the flow channel.

FIG. 1G shows a graph of simulated horizontal and vertical displacements of flow from an intended location as a function of alignment error in the flow focusing microfluidic device 100. Horizontal displacement (darker circles) and vertical displacement (lighter circles) in μm are plotted as a function of the alignment error in μm. As depicted in FIG. 1G, the flow focusing microfluidic device 100 may suffer from slight displacements in the horizontal direction due to alignment errors. However, the flow focusing microfluidic device 100 may suffer from large displacements in the vertical direction due to alignment errors. For instance, an alignment error of only 4 μm causes a vertical displacement of up to 4 μm from the intended location (the center of the flow channel).

Improved Robustness Against Alignment Errors

The present disclosure provides flow focusing microfluidic devices which may have improved robustness against alignment errors. Systems of the present disclosure may be more robust against alignment errors. For instance, devices and systems of the present disclosure may reduce the displacement of flow from the intended locations due to alignment errors. In some examples, devices and systems of the present disclosure may have focused flows that deviated from intended locations or trajectories of such focused flows by less than or equal to about 30%, about 20%, about 10%, about 5%, about 4%, about 3%, about 2%, about 1%, about 0.5%, about 0.1%, or less (e.g., as measured by any deviation in flow streams).

FIG. 2A shows a top view of a schematic for a flow focusing microfluidic device 200 comprising a flow channel and first and second sheath channels having different cross-sections which intersect the flow channel. The difference in cross-sections may reduce the displacement of flow due to alignment errors. The flow focusing microfluidic device 200 may comprise a flow channel 210 configured to direct a fluid from a first point 220 to a second point 230 of a fluid flow path 240. The flow focusing microfluidic device 200 may further comprise a first sheath channel 250 intersecting the flow channel between the first and second points. The first sheath channel may be configured to direct a first sheath fluid along a first sheath flow path 260 across the flow channel. The first sheath fluid may be an aqueous or organic fluid. The first sheath fluid may be miscible with the fluid directed along the flow channel. The first sheath fluid may be immiscible with the fluid directed along the flow channel.

The flow focusing microfluidic device 200 may further comprise a second sheath channel 270 intersecting the flow channel between the first and second points. The second sheath channel may be configured to direct a second sheath fluid along a second sheath flow path 280 across the flow channel. The first sheath channel directing the first sheath fluid may have a different cross section than the second sheath channel directing the second sheath fluid, thereby reducing the displacement of the fluid directed along the fluid flow path. The second sheath fluid may be an aqueous or organic fluid. The second sheath fluid may be miscible with the fluid directed along the flow channel. The second sheath fluid may be immiscible with the fluid directed along the flow channel. The first and second sheath fluids may be the same fluid. In some aspects, the first sheath channel and the second sheath channel may be orthogonal to the flow channel. As shown in FIG. 2A, the first and second sheath fluids may cross the flow channel in opposite directions. The first sheath fluid may flow in a direction orthogonal to the flow channel. The second sheath fluid may flow in a direction orthogonal to the flow channel.

The fluidic devices disclosed herein may have focused flows that deviated from intended locations or trajectories of such focused flows by less than or equal to about 30%, about 20%, about 10%, about 5%, about 4%, about 3%, about 2%, about 1%, about 0.5%, about 0.1%, or less (e.g., as measured by any deviation in flow streams). The focused flows may deviate by less than or equal to about 30%, about 20%, about 10%, about 5%, about 4%, about 3%, about 2%, about 1%, about 0.5%, about 0.1%, or less with alignment errors of up to about 10 μm, up to about 20 μm, up to about 30 μm, up to about 40 μm, or up to about 50 μm. The focused flows may deviate by from 0% to 0.10%, from 0% to 1%, from 0% to 5%, from 0% to 10%, from 0% to 20%, from 0% to 30%, from 0.10% to 0.50%, from 1% to 2%, from 1% to 5%, from 5% to 10%, from 5% to 20%, from 5% to 30%, from 10% to 20%, from 10% to 30%, or from 20% to 30%. The alignment error may be from 0 μm to 1 μm, from 0 μm to 5 μm, from 0 μm to 10 μm, from 0 μm to 20 μm, from 0 μm to 30 μm, from 0 μm to 40 μm, from 1 μm to 2 μm, from 1 μm to 5 μm, from 1 μm to 10 μm, from 5 μm to 10 μm, from 5 μm to 20 μm, from 10 μm to 20 μm, from 10 μm to 30 μm, from 10 μm to 40 μm, from 20 μm to 30 μm, from 20 μm to 40 μm, or from 30 μm to 40 μm.

The flow focusing microfluidic device 200 may be configured such that the first sheath channel is adjacent to or in fluidic contact with the second sheath channel. In some aspects, the flow focusing microfluidic device may be configured such that the first sheath fluid fluidically interacts with or fluidically contacts the second sheath fluid. In some aspects, the flow focusing microfluidic device may be configured such that the first sheath fluid, the second sheath fluid, or both fluidically interact with or fluidically contact the flow channel fluid. The flow focusing microfluidic device 200 may comprise one or more additional sheath channels between the first sheath channel and the second sheath channel. For instance, the flow focusing microfluidic device 200 may comprise third, fourth, fifth, sixth, seventh, eighth, ninth, tenth, or additional sheath channels. Each of the one or more additional sheath channels may intersect the flow channel between the first point and the second point.

The flow focusing microfluidic device 200 may be configured such that the flow channel intersects the first sheath channel at any possible angle. For instance, the flow channel may intersect the first sheath channel at an angle of at least about 0 degrees, at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least 70 about degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more. The flow channel may intersect the first sheath channel at angle of at most about 90 degrees, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degrees, or less. The flow channel may intersect the first sheath channel at an angle that is within a range defined by any two of the preceding values. The flow channel may intersect the first sheath channel at angle of from 0 degrees to 15 degrees, from 0 degrees to 30 degrees, from 0 degrees to 45 degrees, from 0 degrees to 60 degrees, from 0 degrees to 75 degrees, from 0 degrees to 90 degrees, from 15 degrees to 30 degrees, from 15 degrees to 45 degrees, from 15 degrees to 60 degrees, from 15 degrees to 75 degrees, from 15 degrees to 90 degrees, from 30 degrees to 45 degrees, from 30 degrees to 60 degrees, from 30 degrees to 75 degrees, from 30 degrees to 90 degrees, from 45 degrees to 60 degrees, from 45 degrees to 75 degrees, from 45 degrees to 90 degrees, from 60 degrees to 75 degrees, from 60 degrees to 90 degrees, or from 75 degrees to 90 degrees. The flow channel may be orthogonal to the first sheath channel.

The flow focusing microfluidic device may be configured such that the flow channel intersects the second sheath channel at any possible angle. For instance, the flow channel may intersect the second sheath channel at an angle of at least about 0 degrees, at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more. The flow channel may intersect the second sheath channel at angle of at most about 90 degrees, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degrees, or less. The flow channel may intersect the second sheath channel at an angle that is within a range defined by any two of the preceding values. The flow channel may intersect the second sheath channel at angle of from 0 degrees to 15 degrees, from 0 degrees to 30 degrees, from 0 degrees to 45 degrees, from 0 degrees to 60 degrees, from 0 degrees to 75 degrees, from 0 degrees to 90 degrees, from 15 degrees to 30 degrees, from 15 degrees to 45 degrees, from 15 degrees to 60 degrees, from 15 degrees to 75 degrees, from 15 degrees to 90 degrees, from 30 degrees to 45 degrees, from 30 degrees to 60 degrees, from 30 degrees to 75 degrees, from 30 degrees to 90 degrees, from 45 degrees to 60 degrees, from 45 degrees to 75 degrees, from 45 degrees to 90 degrees, from 60 degrees to 75 degrees, from 60 degrees to 90 degrees, or from 75 degrees to 90 degrees. The flow channel may be orthogonal to the second sheath channel.

The flow focusing microfluidic device may be configured such that the first sheath channel intersects the second sheath channel at any possible angle. For instance, the first sheath channel may intersect the second sheath channel at an angle of at least about 0 degrees, at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more. The first sheath channel may intersect the second sheath channel at angle of at most about 90 degrees, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degrees, or less. The first sheath channel may intersect the second sheath channel at an angle that is within a range defined by any two of the preceding values. The first sheath channel may intersect the second sheath channel at angle of from 0 degrees to 15 degrees, from 0 degrees to 30 degrees, from 0 degrees to 45 degrees, from 0 degrees to 60 degrees, from 0 degrees to 75 degrees, from 0 degrees to 90 degrees, from 15 degrees to 30 degrees, from 15 degrees to 45 degrees, from 15 degrees to 60 degrees, from 15 degrees to 75 degrees, from 15 degrees to 90 degrees, from 30 degrees to 45 degrees, from 30 degrees to 60 degrees, from 30 degrees to 75 degrees, from 30 degrees to 90 degrees, from 45 degrees to 60 degrees, from 45 degrees to 75 degrees, from 45 degrees to 90 degrees, from 60 degrees to 75 degrees, from 60 degrees to 90 degrees, or from 75 degrees to 90 degrees. The first sheath channel may be parallel to the second sheath channel.

The fluid may be configured to fluidically interact with the first sheath fluid. The fluid may be configured to fluidically interact with the second sheath fluid. The fluid may be configured to fluidically contact the first sheath fluid. The fluid may be configured to fluidically contact the second sheath fluid. The first and second sheath fluids may be configured to focus the fluid. The first and second sheath fluids may be configured to hydrodynamically focus the fluid.

FIG. 2B shows a side view of the schematic for the flow focusing microfluidic device 200. As shown in FIG. 2B, the flow channel 210 and first and second sheath channels 250 and 270, respectively, may be arranged in a vertically stacked configuration such that the flow channel is located between the first and second sheath channels (e.g., the first sheath channel may be located above the flow channel and the flow channel may be located above the second sheath channel). The first sheath channel may have a first cross-section and the second sheath channel may have a second cross-section. The first cross-section may be different from the second cross-section. The first sheath channel may have a first width 252 and the second sheath channel may have a second width 272. The first width may be different from the second width.

The first width may be at least about 1 μm, at least about 2 μm, at least about 3 μm, at least about 4 μm, at least about 5 μm, at least about 6 μm, at least about 7 μm, at least about 8 μm, at least about 9 μm, at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 20 mm, at least about 30 mm, at least about 40 mm, at least about 50 mm, or more. The first width may be at most about 50 mm, at most about 40 mm, at most about 30 mm, at most about 20 mm, at most about 10 mm, at most about 9 mm, at most about 8 mm, at most about 7 mm, at most about 6 mm, at most about 5 mm, at most about 4 mm, at most about 3 mm, at most about 2 mm, at most about 1 mm, at most about 900 μm, at most about 800 μm, at most about 700 μm, at most about 600 μm, at most about 500 μm, at most about 400 μm, at most about 300 μm, at most about 200 μm, at most about 100 μm, at most about 90 μm, at most about 80 μm, at most about 70 μm, at most about 60 μm, at most about 50 μm, at most about 40 μm, at most about 30 μm, at most about 20 μm, at most about 10 μm, at most about 9 μm, at most about 8 μm, at most about 7 μm, at most about 6 μm, at most about 5 μm, at most about 4 μm, at most about 3 μm, at most about 2 μm, at most about 1 μm, or less. The first width may be within a range defined by any two of the preceding values.

The second width may be at least about 1 μm, at least about 2 μm, at least about 3 μm, at least about 4 μm, at least about 5 μm, at least about 6 μm, at least about 7 μm, at least about 8 μm, at least about 9 μm, at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 20 mm, at least about 30 mm, at least about 40 mm, at least about 50 mm, or more. The second width may be at most about 50 mm, at most about 40 mm, at most about 30 mm, at most about 20 mm, at most about 10 mm, at most about 9 mm, at most about 8 mm, at most about 7 mm, at most about 6 mm, at most about 5 mm, at most about 4 mm, at most about 3 mm, at most about 2 mm, at most about 1 mm, at most about 900 μm, at most about 800 μm, at most about 700 μm, at most about 600 μm, at most about 500 μm, at most about 400 μm, at most about 300 μm, at most about 200 μm, at most about 100 μm, at most about 90 μm, at most about 80 μm, at most about 70 μm, at most about 60 μm, at most about 50 μm, at most about 40 μm, at most about 30 μm, at most about 20 μm, at most about 10 μm, at most about 9 μm, at most about 8 μm, at most about 7 μm, at most about 6 μm, at most about 5 μm, at most about 4 μm, at most about 3 μm, at most about 2 μm, at most about 1 μm, or less. The second width may be within a range defined by any two of the preceding values.

The flow channel may have a flow channel width of at least about 1 μm, at least about 2 μm, at least about 3 μm, at least about 4 μm, at least about 5 μm, at least about 6 μm, at least about 7 μm, at least about 8 μm, at least about 9 μm, at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 2 mm, at least about 3 mm, at least about 4 mm, at least about 5 mm, or more. The flow channel may have a flow channel width of at most about 5 mm, at most about 4 mm, at most about 3 mm, at most about 2 mm, at most about 1 mm, at most about 900 μm, at most about 800 μm, at most about 700 μm, at most about 600 μm, at most about 500 μ, at most about 400 μm, at most about 300 μm, at most about 200 μm, at most about 100 μm, at most about 90 μm, at most about 80 μm, at most about 70 μm, at most about 60 μm, at most about 50 μm, at most about 40 μm, at most about 30 μm, at most about 20 μm, at most about 10 μm, at most about 9 μm, at most about 8 μm, at most about 7 μm, at most about 6 μm, at most about 5 μm, at most about 4 μm, at most about 3 μm, at most about 2 μm, at most about 1 μm, or less. The flow channel may have a flow channel width that is within a range defined by any two of the preceding values.

The ratio of the first width to the flow channel width may be at least about 0.5, at least about 1, at least about 2, at least about 3, at least about 4, at least about 5, at least about 6, at least about 7, at least about 8, at least about 9, at least about 10, at least about 20, or more. The ratio of the first width to the flow channel width may be at most about 20, at most about 10, at most about 9, at most about 8, at most about 7, at most about 6, at most about 5, at most about 4, at most about 3, at most about 2, at most about 1, at most about 0.5, or less. The ratio of the first width to the flow channel width may be within a range that is defined by any two of the preceding values.

The ratio of the second width to the flow channel width may be at least about 0.5, at least about 1, at least about 2, at least about 3, at least about 4, at least about 5, at least about 6, at least about 7, at least about 8, at least about 9, at least about 10, at least about 20, or more. The ratio of the second width to the flow channel width may be at most about 20, at most about 10, at most about 9, at most about 8, at most about 7, at most about 6, at most about 5, at most about 4, at most about 3, at most about 2, at most about 1, at most about 0.5, or less. The ratio of the second width to the flow channel width may be within a range that is defined by any two of the preceding values.

FIG. 2C shows an isometric view of the flow focusing microfluidic device 200.

FIG. 2D shows a side view of the flow focusing microfluidic device 200.

The flow focusing microfluidic device 200 described herein (for instance, with respect to FIG. 2A, FIG. 2B, FIG. 2C, and FIG. 2D) may be manufactured or formed using fabrication, such as microfabrication or nanofabrication. This may include preparing one or more substrate, such as using one or more of solvent cleaning, cleaning using a piranha solution (e.g., mixture of sulfuric acid ($H_2SO_4$) and hydrogen peroxide ($H_2O_2$)), substrate (e.g., wafer) cleaning, ion implantation, ultraviolet photolithography, deep ultraviolet photolithography, extreme ultraviolet photolithography, electron beam lithography, nanoimprint lithography, wet chemical etching, dry chemical etching, plasma etching, reactive ion etching, deep reactive ion etching, electron beam milling, thermal annealing, thermal oxidation, thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, electrochemical deposition, wafer bonding, wire bonding, flip chip bonding, thermosonic bonding, wafer dicing, soft lithography, imprint lithography, microimprint lithography, nanoimprint lithography, injection molding, micromilling, three-dimensional (3D) printing, or any other microfabrication or nanofabrication manufacturing technique. In some examples, 3D printing is fused filament fabrication, such as fused deposition modeling.

The flow focusing microfluidic device 200 may be manufactured or formed using fabrication, such as microfabrication or nanofabrication, applied to at least a first substrate and a second substrate. The first and second substrates may each be subjected to one or more microfabrication or nanofabrication techniques to form one or more of the flow channel, first sheath channel, and second sheath channel. The second substrate may be different from the first substrate. For instance, the flow channel and the first sheath channel may be formed on the first substrate and the second sheath channel may be formed on the second substrate.

The first substrate, the second substrate, or both may be formed of a metal, a metal alloy, a semiconductor, an insulating material, a polymeric material or a composite material. In some examples, the first and second substrates may comprise a material individually selected from the group consisting of: glasses, semiconductors, plastics (e.g., elastomers, such as thermosets or thermoplastics), and metals. The first and second substrates may comprise a material individually selected from the group consisting of: glass, silicon, polydimethylsiloxane (PDMS), poly(methyl methacrylate) (PMMA), polycarbonate, cyclo-olefin copolymer (COC), cyclo-olefin polymer (COP), and aluminum.

The flow focusing microfluidic device 200 may be more robust to non-idealities, such as manufacturing tolerances that result in alignment errors of the first or second sheath, or both, than other flow focusing microfluidic devices. Such alignment errors may result in fewer negative effects on the performance of flow focusing microfluidic device 200 than on the performance of other flow focusing microfluidic devices.

FIG. 2E shows simulated horizontal displacement of flow from an intended location due to misalignments in the flow focusing microfluidic device 200. For the simulation depicted in FIG. 2E, the first and second channels had an alignment error of 40 µm. As depicted in FIG. 2E, the fluid flows along the flow path from the right. Upon interacting with the first and second sheath fluids, the fluid is highly focused on the left. Negligible displacement from the intended location (the center of the flow channel) is evident, as shown by negligible offset of the fluid flow lines from the zero point of the y-axis, representing the center of the flow channel, on the left side of the plot in FIG. 2E. When compared with the simulated vertical displacement of the flow focusing microfluidic device 100 depicted in FIG. 1E, it is evident that the flow focusing microfluidic device 200 of the present disclosure reduces the horizontal displacement due to misalignments.

FIG. 2F shows simulated vertical displacement of flow from an intended location due to alignment error in the exemplary flow focusing microfluidic device 200. For the simulation depicted in FIG. 2F, the first and second channels had an alignment error of 40 µm. As depicted in FIG. 2F, the fluid flows along the flow path from the right. Upon interacting with the first and second sheath fluids, the fluid is highly focused on the left. Slight displacement from the intended location (the center of the flow channel) is evident, as shown by a slight offset of the fluid flow lines from the zero point of the y-axis, representing the center of the flow channel, on the left side of the plot in FIG. 2F. When compared with the simulated vertical displacement of the flow focusing microfluidic device 100 depicted in FIG. 1F, the flow focusing microfluidic device 200 of the present disclosure may reduce the vertical displacement due to misalignments.

FIG. 2G shows a graph of simulated horizontal and vertical displacements of flow from an intended location as a function of alignment error in the flow focusing microfluidic device 200. Horizontal displacement (darker circles) and vertical displacement (lighter circles) in µm are plotted as a function of the alignment error in µm. As depicted in FIG. 2G, the focusing microfluidic device 200 may not suffer from displacements in the horizontal direction due to alignment errors. Moreover, the flow focusing microfluidic device 200 may not suffer from very large displacements in the vertical direction due to alignment errors. For instance, an alignment error of 40 µm causes a vertical displacement of less than 2.5 µm from the intended location (the center of the flow channel), as depicted in FIG. 2G. An alignment error of 40 µm may cause a vertical displacement of less than 10 µm, less than 8 µm, less than 6 µm, less than 4 µm, or less than 2 µm. An alignment error of 20 µm may cause a vertical displacement of less than 10 µm, less than 8 µm, less than 6 µm, less than 4 µm, or less than 2 µm. When compared with the simulated horizontal and vertical displacements of the flow focusing microfluidic device 100 depicted in FIG. 1G, the flow focusing microfluidic device 200 of the present disclosure may reduce the horizontal and vertical displacements due to misalignments.

The system 200 may further comprise a fluid flow unit coupled to one or more of the flow channel, first sheath channel, and second sheath channel. The fluid flow unit may be configured to direct one or more of the fluid through the flow channel, the first sheath fluid through the first sheath channel, and the second sheath fluid through the second sheath channel. The fluid flow unit may comprise one or more pumps. The fluid flow unit may comprise one or more compressors. In some aspects, the one or more pumps, the one or more compressors, or both may be configured to direct one or more of the fluid through the flow channel, the first sheath fluid through the first sheath channel, and the second sheath fluid through the second sheath channel.

Figure 3:
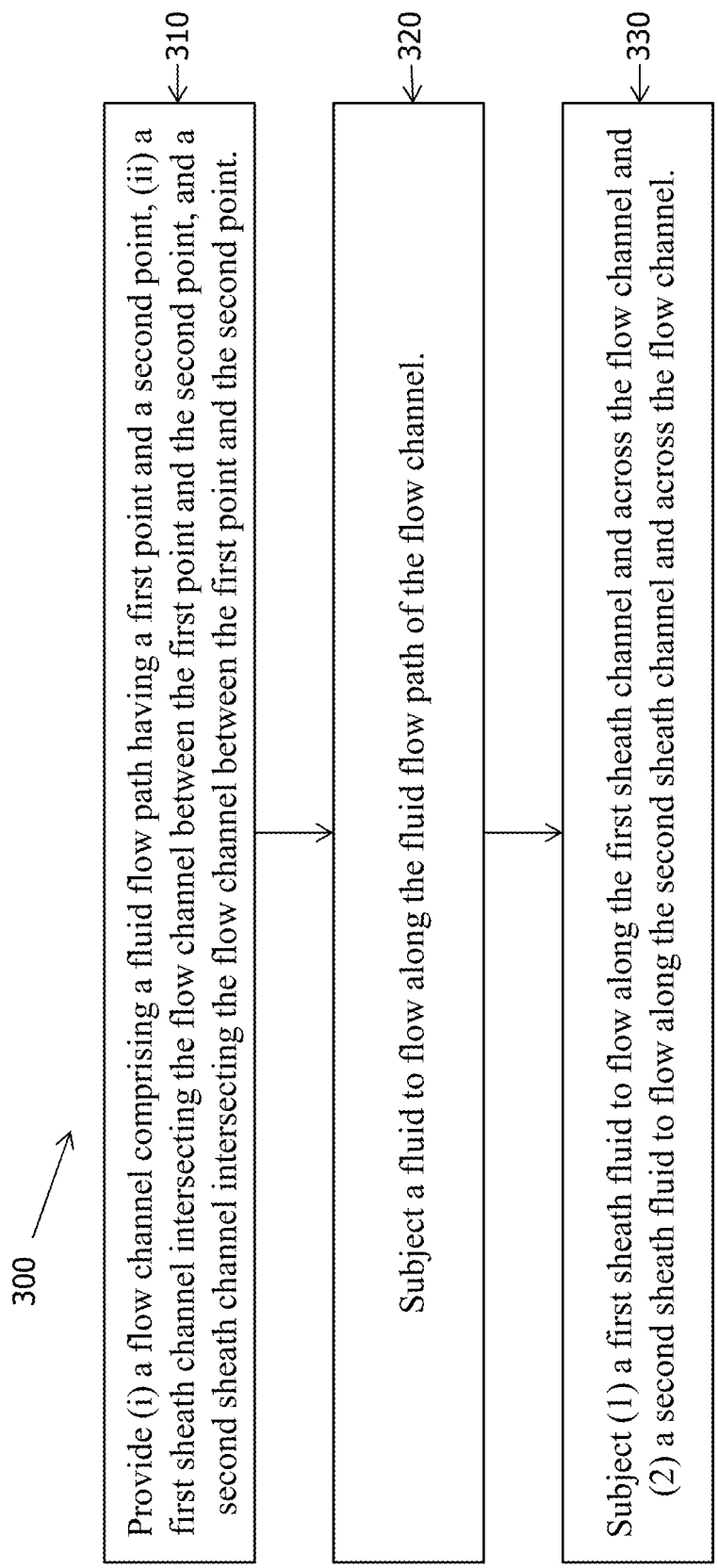
FIG. 3 shows a method for fluid flow focusing.

FIG. 3 shows a method 300 for fluid flow focusing. In a first operation 310, the method may comprise providing (i) a flow channel comprising a fluid flow path having a first point and second point, (ii) a first sheath channel intersecting the flow channel between the first point and the second point, and (iii) a second sheath channel intersecting the flow channel between the first point and the second point. The flow channel may be similar to flow channel 210 described herein. The first point may be similar to first point 220 described herein. The second point may be similar to second point 230 described herein. The fluid flow path may be similar to fluid flow path 240 described herein. The first sheath channel may be similar to first sheath channel 250 described herein. The second sheath channel may be similar to second sheath channel 270 described herein. The second sheath channel may have a different cross-section than the first sheath channel. The first and second sheath channels may have first and second widths, respectively. The first width may be different from the second width. The fluid flow channel and first and second sheath channels may be arranged in any configuration described herein with respect to system 200.

In a second operation 320, the method may comprise subjecting a fluid to flow along the fluid flow path of the flow channel. In some aspects, the fluid may be subjected to flow along the first fluid flow path by a fluid flow unit, as described elsewhere herein.

In a third operation 330, the method may comprise subjecting (1) a first sheath fluid to flow along the first sheath channel and across the flow channel and (2) a second sheath fluid to flow along the second sheath channel and across the flow channel. The first sheath fluid may be any first sheath fluid described herein. The second sheath fluid may be any second sheath fluid described herein. In some aspects, the first sheath fluid, the second sheath fluid, or both may be subjected to flow along the first fluid flow path by a fluid flow unit, as described elsewhere herein. The first and second sheath fluids may hydrodynamically focus the fluid, as described herein.

Figure 4:
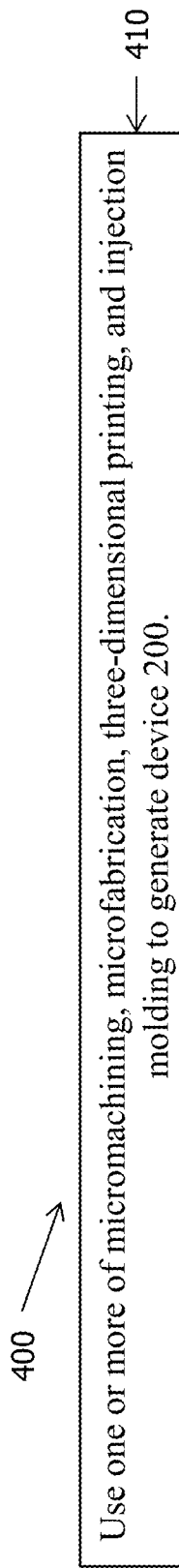
FIG. 4 shows a method for manufacturing a device for fluid flow focusing.

FIG. 4 shows a method 400 for manufacturing a device for fluid flow focusing. In a first operation 410, the method may comprise using fabrication, such as, for example, one or more members selected from the group consisting of micromachining, microfabrication, three-dimensional printing, and injection molding, to generate the device. The device may comprise, for example, the flow focusing microfluidic device 200 described elsewhere herein. The device may comprise a flow channel configured to direct a fluid from a first point to a second point of a fluid flow path. The device may comprise a first sheath channel intersecting the flow channel between the first point and the second point. The first sheath channel may be configured to direct a first sheath fluid across the flow channel. The device may comprise a second sheath channel intersecting the flow channel between the first point and the second point. The second sheath channel may be configured to direct a second sheath fluid across the flow channel. The second sheath channel may have a different cross-section than the first sheath channel. The second sheath channel may have a different width than the first sheath channel.

The flow channel may be similar to flow channel 210 described herein. The first point may be similar to first point 220 described herein. The second point may be similar to second point 230 described herein. The fluid flow path may be similar to fluid flow path 240 described herein. The first sheath channel may be similar to first sheath channel 250 described herein. The second sheath channel may be similar to second sheath channel 270 described herein. The fluid flow channel and first and second sheath channels may be arranged in any configuration described herein with respect to flow focusing microfluidic device 200.

The method may further comprise providing a first substrate and a second substrate. The first substrate may comprise the first sheath channel and the second substrate may comprise the second sheath channel. The method may further comprise bringing the first substrate in contact with the second substrate. The first substrate may be any first substrate described herein. The second substrate may be any second substrate described herein. The first substrate may comprise a first portion of the flow channel and the second substrate may comprise a section portion of the flow channel. The first substrate may comprise the flow channel. The second substrate may comprise the flow channel.

The systems and methods described herein may be used for flow focusing of fluids containing any number of particles, such as cells. The systems and methods may be used to focus the particles into a narrow cross-section in order to enhance downstream analysis of the particles using techniques such as flow cytometry.

Computer Systems

Figure 5:
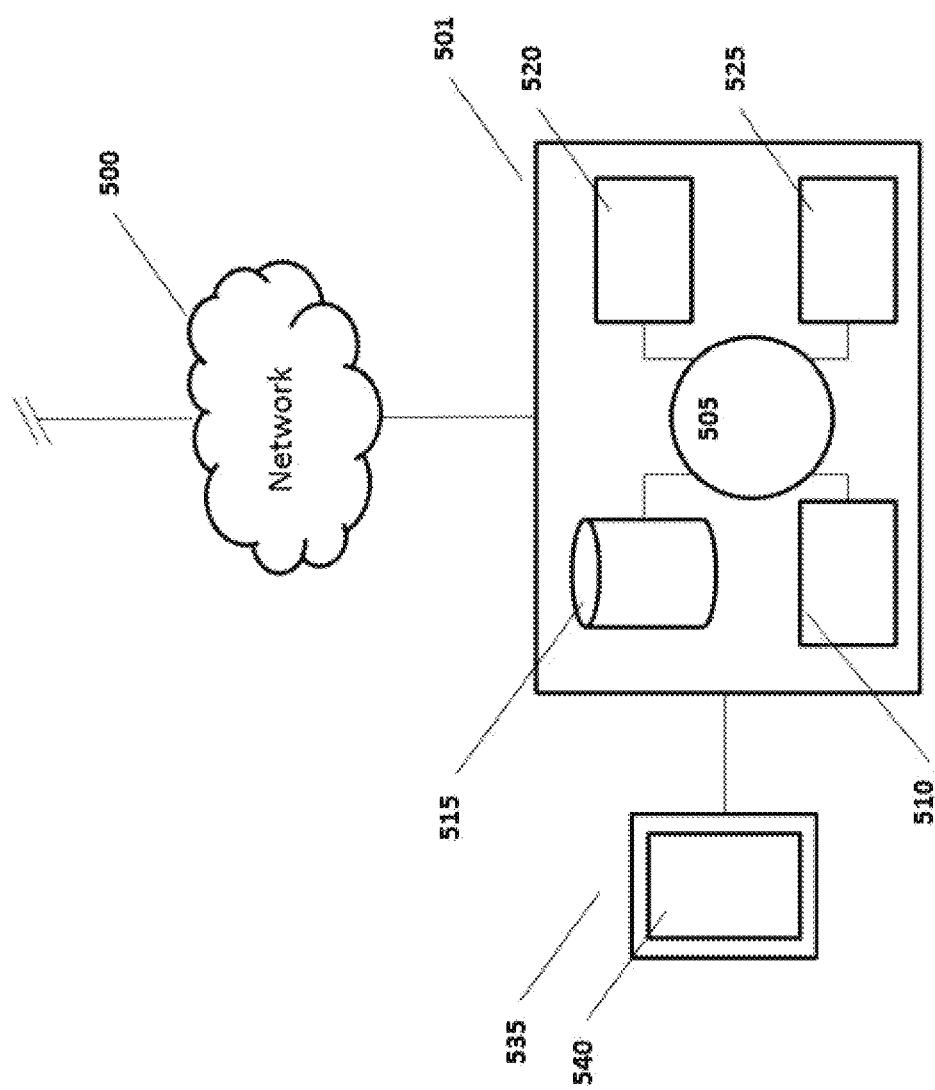
FIG. 5 shows a computer system that is programmed or otherwise configured to operate any of the methods or systems described herein.

The present disclosure provides computer systems for implementing methods and devices of the present disclosure. FIG. 5 shows a computer system 501 that is programmed or otherwise configured to operate any method or system described herein (such as any method or system for flow focusing or any method for manufacturing any flow focusing device described herein). The computer system 501 can regulate various aspects of the present disclosure. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 500 with the aid of the communication interface 520. The network 500 can be the Internet, an internet and/or extranet, or an intranet and/or extranet that is in communication with the Internet. The network 500 in some cases is a telecommunication and/or data network. The network 500 can include one or more computer servers, which can enable distributed computing, such as cloud computing. The network 500, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 500. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants (PDAs). The user can access the computer system 501 via the network 500.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, enact a method for flow focusing as described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for fluid flow focusing, comprising:
   a flow channel configured to direct a fluid flow;
   a first sheath channel intersecting said flow channel, wherein said first sheath channel is configured to direct a first sheath fluid to fluidically interact with said fluid flow, wherein said first sheath channel has a first cross-section, wherein the first cross-section is perpendicular to the direction of said first sheath fluid; and
   a second sheath channel intersecting said flow channel, wherein said second sheath channel is configured to direct a second sheath fluid to fluidically interact with said fluid flow, wherein said second cross-section is perpendicular to the direction of said second sheath fluid, and wherein said second sheath channel has a second cross-section that is different than said first cross-section of said first sheath channel wherein said second cross-section is configured to reduce displacement of said fluid flow through said flow channel relative to a center line of said flow channel due to a misalignment between said first sheath channel and said second sheath channel.

2. The system of claim 1, wherein said fluid flow is vertically displaced no more than 8 µm relative to said center line of said flow channel when said first sheath channel and said second sheath channel are misaligned by no more than 40 micrometers.

3. The system of claim 1, further comprising a fluid flow unit coupled to one or more of said flow channel, said first sheath channel, and said second sheath channel, wherein said fluid flow unit is configured to direct one or more of said fluid flow through said flow channel, said first sheath fluid through said first sheath channel, and said second sheath fluid through said second sheath channel.

4. The system of claim 3, wherein said fluid flow unit comprises one or more pumps, one or more compressors, or both.

5. The system of claim 1, wherein said flow channel and said first and second sheath channels are arranged in a vertically stacked configuration such that said flow channel is located between said first sheath channel and said second sheath channel.

6. The system of claim 1, wherein said flow channel is orthogonal to said first sheath channel, said second sheath channel, or both.

7. The system of claim 1, wherein said first sheath fluid and said second sheath fluid are configured to hydrodynamically focus said fluid flow.

8. The system of claim 1, wherein said flow channel comprises a flow channel width of at most 2 millimeters (mm).

9. The system of claim 1, wherein said first sheath channel comprises a first sheath channel width, and said second sheath channel comprises a second sheath channel width, and said first sheath channel width, said second sheath channel width, or both are at most 20 millimeters (mm).

10. The system of claim 1, wherein said first sheath channel is formed on a first substrate and said second sheath channel is formed on a second substrate that is different from said first substrate.

11. The system of claim 10, wherein a first portion of the flow channel is formed on said first substrate and a second portion of the flow channel is formed on said second substrate.

12. The system of claim 10, wherein said flow channel is formed on said first substrate.

13. The system of claim 10, wherein said flow channel is formed on said second substrate.

14. The system of claim 10, wherein said first substrate and said second substrate comprise a material individually selected from the group consisting of: glasses, semiconductors, elastomers, plastics, and metals.

15. The system of claim 14, wherein said first substrate and said second substrate comprise a material individually selected from the group consisting of: glass, silicon, polydimethylsiloxane (PDMS), poly(methyl methacrylate) (PMMA), polycarbonate, cyclo-olefin copolymer (COC), cyclo-olefin polymer (COP), and aluminum.

16. The system of claim 1, wherein said first sheath fluid and said second sheath fluid are the same fluid.

17. The system of claim 1, wherein said first sheath channel is adjacent to said second sheath channel.

18. The system of claim 1, further comprising one or more additional sheath channels.

19. The system of claim 1, wherein said system is manufactured using one or more methods selected from the group consisting of: micromachining, three-dimensional printing, and injection molding.

20. A method for fluid flow focusing, comprising:
(a) providing a system comprising: (i) a flow channel configured to direct a fluid flow; (ii) a first sheath channel intersecting said flow channel, wherein said first sheath channel has a first cross-section; and (iii) a second sheath channel intersecting said flow channel, wherein said second sheath channel has a second cross-section that is different than said first cross-section of said first sheath channel, wherein said second cross-section is configured to reduce displacement of said fluid flow through said flow channel relative to a center line of said flow channel due to a misalignment between said first sheath channel and said second sheath channel;
(b) subjecting a fluid to flow along said flow channel; and
(c) subjecting (1) a first sheath fluid to flow along said first sheath channel and fluidically interact with said fluid flowing along said flow channel, wherein said first cross-section is perpendicular to the direction of said first sheath fluid, and (2) a second sheath fluid to flow along said second sheath channel and fluidically interact with said fluid flowing along said flow channel, wherein said second cross-section is perpendicular to said direction of said second sheath fluid.

21. The method of claim 20, wherein said first sheath fluid and said second sheath fluid flow in opposite directions.

22. The method of claim 20, wherein said first sheath fluid and said second sheath fluid hydrodynamically focus said fluid flowing along said flow channel.

23. The system of claim 1, wherein said first sheath channel intersecting said flow channel is configured such that said first sheath channel intersects said flow channel at an angle greater than 0 degrees or wherein said second sheath channel intersecting said flow channel is configured such that said second sheath channel intersects said flow channel at an angle greater than 0 degrees.

24. The method of claim 20, wherein said first sheath channel intersecting said flow channel is configured such that said first sheath channel intersects said flow channel at an angle greater than 0 degrees or wherein said second sheath channel intersecting said flow channel is configured such that said second sheath channel intersects said flow channel at an angle greater than 0 degrees.

* * * * *